US006890946B2

(12) United States Patent
Nakshatri et al.

(10) Patent No.: US 6,890,946 B2
(45) Date of Patent: May 10, 2005

(54) USE OF PARTHENOLIDE TO INHIBIT CANCER

(75) Inventors: Harikrishna Nakshatri, Indianapolis, IN (US); Christopher J. Sweeney, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 10/178,054

(22) Filed: Jun. 21, 2002

(65) Prior Publication Data

US 2003/0125373 A1 Jul. 3, 2003

Related U.S. Application Data

(63) Continuation of application No. PCT/US00/34469, filed on Dec. 19, 2000.

(60) Provisional application No. 60/173,023, filed on Dec. 23, 1999, and provisional application No. 60/173,024, filed on Dec. 23, 1999.

(51) Int. Cl.[7] .......................... A01N 43/36; A61K 31/415

(52) U.S. Cl. .......................... 514/400; 514/449; 514/510; 514/468; 424/464

(58) Field of Search .......................... 514/400, 449, 514/510, 468, 469; 424/464

(56) References Cited

U.S. PATENT DOCUMENTS

| | | | | |
|---|---|---|---|---|
| 5,514,555 A | | 5/1996 | Springer et al. | 435/7.24 |
| 5,919,815 A | * | 7/1999 | Bradley et al. | 514/449 |
| 5,919,816 A | * | 7/1999 | Hausheer et al. | 514/449 |
| 6,410,516 B1 | | 6/2002 | Baltimore et al. | 514/44 |

FOREIGN PATENT DOCUMENTS

| | | | |
|---|---|---|---|
| WO | WO 96/22774 | 8/1996 | |
| WO | WO-9933463 A1 | 7/1999 | A61K/31/365 |

OTHER PUBLICATIONS

Hehner et al., Sesquiterpene Lactones Specifically Inhibit Activation of NF–RB by Preventing the Degradation of IRB–I and IRB–J. The Journal of Biological Chemistry, vol. 273, No. 3, Jan. 16, 1998, pp. 1288–1297.*

Bork, P..M. ,et al. ,"Sesquiterpene lactone containing Mexican Indian medicinal plants and pure sesquiterpene lactones as potent inhibitors of transcription factor NF–kB", *FEBS Lett., vol. 402,No. 1, Database Derwent Drug file on STN, Derwent Information Limited, No. 1997–09449*, (1997), 85–90.

Hehner, Steffen.P. ,et al. ,"Sesquiterpene lactones specifically inhibit activation of NF–kB by preventing the degradation of lkB–alpha and lkB–beta",*J. Biol. Chem., vol. 273, No. 3, Database Chemical Abstracts on STN, American Chemical Society, No. 128:200703*, (1998), 1288–1297 CTO Oct. 20, 2003.

Hehner, Steffen.P. ,et al. ,"The antiInflammatory Sesquiterpene lactone parthenolide inhibits NF–kB by targeting the lkB kinase complex", *J. immunol. vol. 163, No. 10, Database Chemical Abstracts on STN, American Chemical Society No. 132:44670*, (1999),5617–5623.

Hwang, Daniel.,et al. ,"Inhibition of the expression of inducible cyclooxygenase and proinflammatory cytokines by sesquiterpene lactones in macrophages correlates with the inhibition of MAP kinases", *Biochem., Biophys. Res. Commun., vol. 226, No. 3, Database Chemical Abstracts on STN, American Chemical Society, No. 125:273221*, (1996),810–818.

Ross, Jonathan.J. ,et al. ,"Low concentrations of the feverfew component parthenolide inhibit in vitro growth of tumor lines in a cytostatic fashion", *Planta Med., vol. 65, No. 2, Database Chemical Abstracts on STN, American Chemical Society, No. 120:232122*, (1999),126–129.

Wiedhopf, R..M. ,et al. ,"Tumor inhibitory agent from *Magnolia grandiflora* (Magnoliaceae) 1. Parthenolide", *J. Pharm. Sci., vol. 62, No. 2, Database Chemical Abstracts on STN, American Chemical Society, No. 78:115152*, (1973), 345.

Woynarowski, Jan.M. ,et al. ,"Inhibitors of DNA biosynthesis in HeLa cells by cytotoxic antitumor sesquiterpene lactones", *Mol. PHaarmacol., vol. 19, No. 1, Database Chemical Abstracts on STN, American Chemical Society, No. 94:150059*, (1981),97–102.

Baldwin, et al., "The NF–kB and lkB Proteins: New Discoveries and Insights", *Annual Review of Immunology, 14 ISSN: 0732–0582*, (1996),649–683.

Iruela–Arispe, M. L., et al., "Angiogenesis: A Dynamic balance of Stimulators and Inhibitors", *Thrombosis and Haemostasis, 78 (1) ISSN: 0340–6245*, (1997),672–677.

Jain, N. K., et al., "Antinociceptive and anti–inflammatory effects of *Tanacetum parthenium* L. extract in mice and rats", *Journal of Ethnopharmacology, 68 (1–3) ISSN: 0378–8741*, (1999),251–259.

Mondranondra, I. O., et al., "Sesquiterpene Lactones and other constituents from a Cytotoxic Extract of Michelia–Floribunda", *Pharmaceuticat Research, 7, (12) ISSN: 0724–8741*, (1990),1269–1272.

Patel, N. M., et al., "Paclitaxel Sensitivity of Breast Cancer Cells with Constitutively active NF–KappaB is enchanged by IkappaBalpha super–repressor and parthenolide", *Oncogene, 19 (36) ISSN: 0950–9232*, (Aug. 24, 2000),4159–4169.

Robles, M. , et al., "Recent studies on the Zoopharmacognosy, Pharmacology and Neurotoxicology of Sesquiterpene Lactones",*Planta Medica, 61 (3) ISSN: 0032–0943*, (1995), 199–203.

(Continued)

*Primary Examiner*—Frederick Krass
*Assistant Examiner*—Amy A. Lewis
(74) *Attorney, Agent, or Firm*—Schwegman, Lundberg, Woessner & Kluth, P.A.

(57) ABSTRACT

The invention provides a method comprising the use of parthenolide, including its analogs, to treat cancer or conditions characterized by abnormal angiogenesis.

19 Claims, 7 Drawing Sheets

OTHER PUBLICATIONS

Sharma, H. W., et al., "The NF–Kappab Transcription Factor in Oncogenesis", *Anticancer Research, Helenic anticancer Institute, 16 ISSN: 0250–7005*, (Mar. 1996),589–596.

Yoshida et al., "Suppression of Retinal Neovascularization by the NF–αB Inhibitor Pyrrolidine Dithiocarbamate in Mice", *Investigative Ophthalmology & Visual Science, 40*, 1624–1629 (1999).

* cited by examiner

USE OF PARTHENOLIDE TO INHIBIT CANCER

CROSS-REFERENCE TO RELATED APPLICATIONS

The present application is a continuation under 35 USC 111(a) of PCT/US00/34469 filed Dec. 19, 2000 (WO 01/45699), which claims priority under 35 U.S.C. §120 to U.S. provisional patent application Ser. No. 60/173,023, filed Dec. 23, 1999 and Ser. No. 60/173,024 filed Dec. 23, 1999, which are incorporated by reference herein.

BACKGROUND OF THE INVENTION

Fatality in cancer is generally due to metastasis and development of resistance to chemotherapy (Fisher, 1994; Liotta et al., 1991). Metastasis and resistance to chemotherapy are mostly due to overexpression of pro-metastatic, pro-angiogenic, multi-drug resistance and anti-apoptotic genes (Baldini, 1997; Fisher, 1994; Wang et al., 1999a). The expression of a significant number of these genes is regulated by NF-κB, Activator Protein (AP-1) and the Ets family of transcription factors (Baeuerle & Henkel, 1994; Grumont et al., 1999; Gutman & Wasylyk, 1990; Lee et al., 1999; Wang et al., 1999b; Wang et al., 1998; Zong et al., 1999).

Expression of the pro-metastatic genes interleukin-6 (IL-6), urokinase plasminogen activator, matrix metalloproteinase 9, the pro-angiogenic gene IL-8 and the anti-apoptotic genes c-IAP1, cIAP2, TRAF1, TRAF2, Bfl-1/A1, Bcl-$X_L$, and Mn-SOD is induced by NF-κB (Baeuerle & Henkel, 1994; Grumont et al., 1999; Jones et al., 1997; Lee et al., 1999; Wang et al., 1999b, Wang et al., 1998; Zong et al., 1999). Normally, NF-κB resides in the cytoplasm in an inactive state bound to IκB proteins (Baeuerle & Henkel, 1994). When cells are exposed to TNFα, IL-1 or chemotherapeutic agents, a multisubunit IκB kinase complex (IKC) is activated, which phosphorylates IκBs (Zandi & Karin, 1999). NF-κB dissociates from phosphorylated IκBs, translocates to the nucleus and activates target genes (Baeuerle & Henkel, 1994). The ability of activated NF-κB to induce gene expression depends on the cell type and the type of NF-κB inducer.

For example, in cell types that are sensitive to TNFα and chemotherapy-induced apoptosis, NF-κB is inactivated by caspases and the induction of NF-κB-dependent cell survival signals is markedly reduced (Levkau et al., 1999). In contrast, activation of NF-κB by growth factors or IL-1 can cause an increase in anti-apoptotic gene expression and subsequent resistance to TNF and chemotherapy (Wang et al., 1996). Inhibition of NF-κB activation by IκB overexpression can convert TNF- and chemotherapy-resistant cells to a sensitive phenotype (Beg & Baltimore, 1996; Van Antwerp et al., 1996; Wang et al., 1996).

Recent studies indicate that NF-κB is constitutively active in a number of tumors including Hodgkin's lymphoma, melanoma, juvenile myelomonocytic leukemia, cutaneous T cell lymphoma, melanoma, squamous cell carcinoma and Bcr-Abl-induced transformation (Bargou et al., 1997; Dong et al., 1999; Giri & Aggarwal, 1998; Reuther et al., 1998; Shattuck-Brandt & Richmond, 1997). Constitutive NF-κB activation has been described in a subset of breast cancers (Cogswell et al., 2000; Nakshatri et al., 1997; Sovak et al., 1997).

Although a number of drugs, including aspirin, have been described as having some ability to prevent NF-κB activation (Yin et al., 1998), a need exists for compounds that can potently inhibit NF-κB activation at clinically achievable doses. Such drugs can be used as primary or adjunct therapeutic agents in the treatment of cancer, or in other pathologies involving NF-κB activation.

SUMMARY OF THE INVENTION

In one aspect, the present invention provides a therapeutic method to treat cancer, including hematological malignancies and solid tumors, such as prostate cancer, ovarian cancer, breast cancer, brain cancer and hepatic cancer, comprising administering to a mammal afflicted with said cancer an amount of parthenolide, or an analog thereof that is an NF-κB inhibitor, effective to inhibit the viability of cancer cells of said mammal. The parthenolide may be administered as primary therapy, or as adjunct therapy, either following local intervention (surgery, radiation, local chemotherapy) or in conjunction with at least one other chemotherapeutic agent.

The present invention also provides a method of increasing the susceptibility of human cancer cells to a chemotherapeutic agent comprising contacting the cells with an effective sensitizing amount of parthenolide. Thus, the invention provides a therapeutic method for the treatment of a human or other mammal afflicted with cancer, wherein an effective amount of parthenolide is administered to a subject afflicted with said cancer and that may be undergoing, or be about to undergo, treatment with a chemotherapeutic ("antineoplastic") agent. As used herein, the term "parthenolide" includes essentially pure parthenolide, as described below, or analogs exhibiting useful NF-κB and/or c-IAP2 inhibitory activity that are known or apparent to the art.

Preferably, parthenolide is administered in conjunction with one or more chemotherapeutic agents effective against the particular cancer such as gemcitabine or 5-FU, if pancreatic cancer is being treated, tamoxifen or paclitaxel, if breast cancer is to be treated, leuprolide or other anti-androgens, if prostate cancer is involved, and the like.

In another aspect, the present invention comprises a therapeutic method comprising the administration of parthenolide to treat non-tumorigenic angiogenesis-dependent diseases that are characterized by the abnormal growth of blood vessels. Parthenolide may also be utilized in surgical procedures in which anti-angiogenesis is useful, including stent and graft placement and in the treatment of tumor excision sites.

The present invention also provides a method to determine whether or not a cancer patient will be amenable to treatment by a NF-κB inhibitor, alone or in combination with one or more other chemotherapeutic agents, comprising (a) isolating a portion of cancer cells from said patient, and (b) determining whether said cells comprise constitutively active NF-κB and/or express c-IAP2; and correlating the level of NF-κB and/or c-IAP2 with the ability of the inhibitor to inhibit NF-κB or c-IAP2 in reference cells of said cancer that also comprise NF-κB or c-IAP2. This method is based on the fact that a high level of NF-κB activity and/or overexpression of c-IAP2 is indicative of susceptibility of said cancer cells to a NF-κB inhibitor. Thus, a cancer patient about to undergo, or undergoing, treatment for cancer can be rapidly evaluated to see if he/she will benefit from concurrent chemotherapy and administration of parthenolide or an analog thereof.

The terms "high level" and "overexpression" are defined by reference to the assays and test data set forth hereinbelow, e.g., a "++" or greater rating on Table 1. For example, it can readily be determined empirically, and by in vitro tests, if a population of cancer cells, such as a population isolated from a cancer patient, exhibits an NF-κB level or overexpresses the c-IAP2 gene to the extent required to render the cancer susceptible to treatment in accord with the present invention.

DETAILED DESCRIPTION OF THE INVENTION

Figure 1:
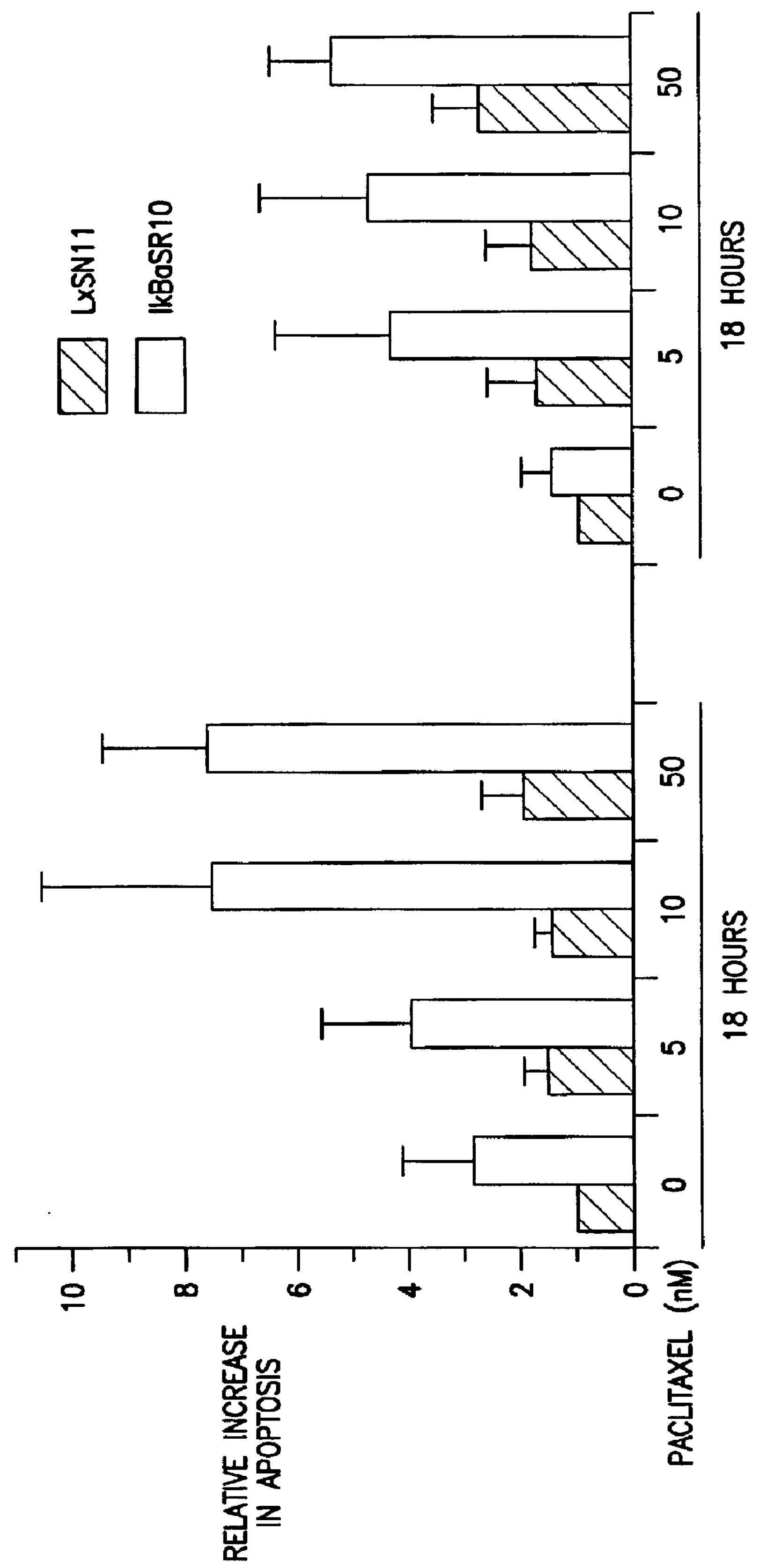
FIG. 1 is a graph showing the relative difference in apoptosis among cell types LxSN11 and IxBαSR10 with or without paclitaxel treatment. A population of $5\times10^4$ LxSN11 and IxBαSR10 cells were grown overnight and incubated with paclitaxel for 18 and 48 hrs. Apoptosis was measured by ELISA. The rate of spontaneous apoptosis in untreated LxSN11 cells was set as one unit.

Parthenolide, ([1aR-(1αR*, 4E, 7aS*, 10αS*, −10bR*)]-2, 3, 6, 7, 7α, 8, 10α, 10b-Octahydro-1α, 5-dimethyl-8-methyleneoxireno[9, 10]cyclodeca[1, 2-b]furan-9(1αH)-one) or 4,5α-epoxy-6β-hydroxy-germacra-1(10), 11(13)-dien-12-oic acid γ-lactone is a sesquiterpene lactone found in feverfew, and in other plants. Its formula is given below:

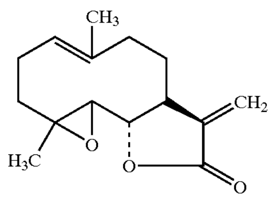

Isolation from *Chrysanthemum parthenium* (L.) Bernh. Compositae and characterization has been described by V. Herout et al., *Chem. & Ind.* (London), 1069 (1959); M. Soucek et al., *Coll. Czech. Chem. Comm.,* 26, 803 (1961). Its isolation from *Magnolia grandiflora* L., *Magnoliaceae* has been described by F. S. El-Feraly, Y. -M. Chan, *J. Pharm. Sci.,* 67, 347 (1978). The absolute configuration was determined by A. S. Bawdekar et al., *Tetrahedron Letters,* 1225 (1966). Its cytotoxicity was investigated by K. -H. Lee et al., *Cancer Res.,* 31, 1649 (1971) and by L. A. J. O'Neill et al., *Brit. J. Clin. Pharmacol,* 23, 81 (1987).

Parthenolide is commercially available as 500 mcg tablets from Ashbury Biologicals and is available as an herbal remedy for migraines in Canada (Murphy et al., 1988). E. Johnson et al., in U.S. Pat. No. 4,758,433, disclose that a parthenolide-containing extract can be used to treat migraine, arthritis and "bronchial complaints." D. H. Hwang et al. (U.S. Pat. No. 5,905,089) disclose that parthenolide can be used to treat or prevent symptoms of "severe inflammatory disorders" associated with the production of various pro-inflammatory "cytokines, chemokines and proteins," including COX-2, MAPKS and NF-κB.

In toxicity studies, parthenolide has been given to rats and dogs at dosages of from about 250–2500 mg/kg/day without significant toxicity. In a phase I study of parthenolide in human patients with cancer, such as incurable prostate cancer, patients can be dosed at 1000 mcg/day, and each subsequent cohort will receive a 30% increase in the dose, for two cycles (8 weeks) of therapy at their assigned dose. Such dosages can also be used to treat and develop treatments for other cancers and angiogenesis-dependent conditions, such as those described hereinbelow, as can doses presently used to treat migraine headaches in humans. Dosages suitable for human administration can be calculated from dosages effective in animal models as disclosed in U.S. Pat. No. 5,294,430.

Cancers treatable by the present therapy include the solid and hematological tumors discussed hereinabove, as well as the solid tumors disclosed in U.S. Pat. No. 5,514,555. Hematological cancers, such as the leukemias are disclosed in the *Mayo Clinic Family Health Book,* D. E. Larson, ed., William Morrow, N.Y. (1990) and include CLL, ALL, CML and the like.

Within another aspect of the present invention, methods are provided for inhibiting angiogenesis in patients with non-tumorigenic, angiogenesis-dependent diseases, comprising administering a therapeutically effective amount of a composition comprising parthenolide to a patient with a non-tumorigenic angiogenesis-dependent disease, such that the formation of new blood vessels is inhibited. Within other aspects, methods are provided for inhibit reactive proliferation of endothelial cells or capillary formation in non-tumorigenic, angiogenesis-dependent diseases, such that the blood vessel is effectively occluded. Within one embodiment, the anti-angiogenic composition comprising parthenolide is delivered to a blood vessel which is actively proliferating and nourishing a tumor.

In addition to tumors, numerous other non-tumorigenic angiogenesis-dependent diseases, which are characterized by the abnormal growth of blood vessels, may also be treated with the anti-angiogenic parthenolide compositions, or anti-angiogenic factors of the present invention. Anti-angiogenic parthenolide compositions of the present invention can block the stimulatory effects of angiogenesis promoters, reducing endothelial cell division, decreasing endothelial cell migration, and impairing the activity of the proteolytic enzymes secreted by the endothelium. Representative examples of such non-tumorigenic angiogenesis-dependent diseases include corneal neovascularization, hypertrophic scars and keloids, proliferative diabetic retinopathy, arteriovenous malformations, atherosclerotic plaques, delayed wound healing, hemophilic joints, non-union fractures, Osler-Weber syndrome, psoriasis, pyogenic granuloma, scleroderma, trachoma, menorrhagia, retrolental fibroplasia and vascular adhesions. The pathology and treatment of these conditions is disclosed in detail in published PCT application PCT/CA94/00373 (WO 95/03036), at pages 26–36. Topical or directed local administration of the present compositions is often the preferred mode of administration of therapeutically effective amounts of parthenolide, i.e., in depot or other controlled release forms.

Anti-angiogenic compositions of the present invention may also be utilized in a variety of other manners. For example, they may be incorporated into surgical sutures in order to prevent stitch granulomas, implanted in the uterus (in the same manner as an IUD) for the treatment of menorrhagia or as a form of female birth control, administered as either a peritoneal lavage fluid or for peritoneal implantation in the treatment of endometriosis, attached to a monoclonal antibody directed against activated endothelial cells as a form of systemic chemotherapy, or utilized in diagnostic imaging when attached to a radioactively labelled monoclonal antibody which recognizes active endothelial cells.

The magnitude of a prophylactic or therapeutic dose of parthenolide, an analog thereof or a combination thereof, in the acute or chronic management of cancer, i.e., prostate or breast cancer, will vary with the stage of the cancer, such as the solid tumor to be treated, the chemotherapeutic agent(s) or other anti-cancer therapy used, and the route of administration. The dose, and perhaps the dose frequency, will also vary according to the age, body weight, and response of the individual patient. In general, the total daily dose range for parthenolide and its analogs, for the conditions described herein, is from about 0.5 mg to about 2500 mg, in single or divided doses. Preferably, a daily dose range should be about 1 mg to about 100 mg, in single or divided doses, most preferably about 5–50 mg per day. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective amount" or "an effective sensitizing amount" are encompassed by the above-described dosage amounts and dose frequency schedule.

Any suitable route of administration may be employed for providing the patient with an effective dosage of parthenolide. While it is possible that, for use in therapy, parthenolide or its analogs may be administered as the pure chemicals, as by inhalation of a fine powder via an insufflator, it is preferable to present the active ingredient as a pharmaceutical formulation. The invention thus further provides a pharmaceutical formulation comprising parthenolide or an analog thereof, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof, such as a human patient or domestic animal.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the agent from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof. The polymer matrix can be coated onto, or used to form, a medical prosthesis, such as a stent, valve, shunt, graft, or the like.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing, in addition to the active ingredient, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the compounds can be administered as drops, gels (see, S. Chrai et al., U.S. Pat. No. 4,255,415), gums (see S. -L. Lin et al., U.S. Pat. No. 4,136,177) or via a prolonged-release ocular insert.

The invention will be further described by reference to the following detailed examples wherein the following materials and methods were employed:

A. Breast Cancer Cell Lines. All breast cancer cell lines were purchased from the American Type Tissue Culture Collection (Rockville, Md.) and grown as described previously (Bhat-Nakshatri et al., 1998). Wild type and p65−/−fibroblast cells were a gift from D. Baltimore and A. Hoffmann (Beg & Baltimore, 1996).

B. Generation of MDA-MB-231 Cells Overexpressing IκBα Super-Repressor. IκBα super-repressor (IκBαSR) plasmid containing S32A and S36A mutation of IκBα was generated by PCR mediated site-directed mutagenesis and cloned into the EcoRI site of the modified retrovirus vector LxSN (Miller & Rosman, 1989; Wang et al., 1996). Retrovirus and stable IκBαSR expressing MDA-MB-231 clones were prepared as described previously (Newton et al., 1999).

C. Electrophoretic Mobility Shift Assays (EMSAs). Whole cell extracts were prepared and subjected to EMSA with NF-κB and SP-1 probes (Promega, Madison, Wis.) (Newton et al., 1999). Nuclear extracts were prepared as described previously (Dignam et al., 1983). Antibodies for supershift assays were purchased from Santa Cruz Biotechnology (CA) or Upstate Biotechnology (NY).

D. Western Blotting. Total cell lysates were prepared in radioimmunoassay buffer and subjected to Western blotting as described previously (Newton et al., 1999). IκBα and Mn-SOD antibodies were purchased from Santa Cruz Biotechnology (CA) and Upstate Biotechnology, respectively.

E. Northern Blotting and RNase Protection. Total RNA was subjected to Northern blotting as described previously (Newton et al., 1999). Twenty μgs of RNA were subjected to RNase protection using the hAPO-5 probe (PharMingen, San Diego, Calif.) as described by the manufacturers.

F. Drug Treatment, Cell Death Assays, Apoptosis Assay and PARP Cleavage. For cell death assays, $2\times10^3$ cells grown overnight on a 96-well plate were treated with paclitaxel and/or parthenolide (dissolved in ethanol). In combination treatment, parthenolide was added 4 h before paclitaxel treatment. Cell death was measured 18 h after paclitaxel treatment using the MTS assay (Promega, Madison, Wis.). Apoptosis was measured by a histone-ELISA (Roche Diagnostics, Indianapolis, Ind.). $5\times10^4$ cells grown overnight on six well plates were treated with paclitaxel for indicated times. Histone-DNA complexes in the supernatant were detected by ELISA. For the PARP cleavage assay, $5\times10^5$ cells were exposed to the indicated drugs for 24 h. Both adherent and non-adherent cells were collected, lysed in urea-sodium dodecyl sulfate buffer and subjected to Western blotting with PARP antibody (Enzyme System Products, Livermore, Calif.) (Panvichian et al., 1998).

G. Flow Cytometry. $5\times10^5$ cells grown overnight were treated with the indicated concentrations of paclitaxel for 18 h. Cells were collected by trypsinization, washed in phosphate-buffered saline and resuspended in 125 μl of 2 μgs/ml RNase and 300 μl of propidium iodide containing buffer (50 μg/ml propidium iodide, 1 mg/ml sodium citrate, 0.03% NP40). The amount of propidium iodide incorporated was determined by FAScan analysis and the cell cycle distribution was determined using ModFit computer Software. Cell cycle distribution analysis was performed in a single blinded manner. Only diploid cells were considered while calculating the percentage of cells at each phase of cell cycle.

H. Statistical Analysis. In synergy experiments, dose response curves for single agents were generated first. The effect of combined treatment was analyzed by the Isobole method (Berenbaum, 1981).

EXAMPLE 1

Constitutive NF-κB Activation in Breast Cancer Cells Correlates with Increased c-IAP2 and Mn-SOD Expression Previously, it was demonstrated that constitutive NF-κB DNA binding activity varies among breast cancer cell lines (Nakshatri et al., 1997; Newton et al., 1999). As shown in Table 1, the binding activity observed was MDA-MB-436≧HBL100>MDA-MB-231≧MDA-MB-468≧MDA-MB-435>SK-BR-3≧Hs578T≧ZR-75-1>T47-D≧MCF-7 cells (Newton et al., 1999).

TABLE 1

Summary of NF-κB DNA binding activity, C-IAP2 and Mn-SOD Expression in breast cancer cell lines. NF-κB DNA binding activity in these cells has been described (Newton et al., 1999). Relative expression of c-IAP2 and Mn-SOD was calculated by densitometric scanning of autoradiograms.

| Cell lines | NF-κB | c-IAP2 | Mn-SOD |
|---|---|---|---|
| MCF-7 | + | − | + |
| T47D | + | − | − |

TABLE 1-continued

Summary of NF-κB DNA binding activity, C-IAP2 and Mn-SOD Expression in breast cancer cell lines. NF-κB DNA binding activity in these cells has been described (Newton et al., 1999). Relative expression of c-IAP2 and Mn-SOD was calculated by densitometric scanning of autoradiograms.

| Cell lines | NF-κB | c-IAP2 | Mn-SOD |
|---|---|---|---|
| ZR-75-1 | ++ | − | − |
| MDA-MB-231 | +++ | +++++ | +++ |
| MDA-MB-435 | +++ | ± | ++ |
| MDA-MB-436 | ++++ | +++ | +++++ |
| MDA-MB-468 | +++ | ++ | ++ |
| SK-BR-3 | ++ | − | + |
| Hs578T | ++ | − | + |
| HBL100 | ++++ | ++ | +++ |

Among these cells, MCF-7, T47D and ZR-75-1 cells are estrogen receptor alpha (ERα)-positive (Sommers et al., 1994). In ERα-positive breast cancer cells, transcriptional activity but not DNA binding activity of NF-κB is inhibited by ERα (Galien & Garcia, 1997; Nakshatri et al., 1997).

Thus, ERα-negative breast cancer cells with higher levels of constitutive NF-κB DNA binding activity may overexpress NF-κB-inducible genes compared to ERα-positive breast cancer cells. To address this possibility, RNase protection assays, Northern analysis, cDNA microarray and differential display methods were used to identify NF-κB regulated genes in breast cancer cells. The RNase protection assay was performed with hAPO-5 probe, which allows quantitation of xIAP, TRAF1, TRAF2, CART, NIAP, c-IAP1, c-IAP2, TRPM2 and CRAF genes. Among these genes, xIAP, TRAF1, TRAF2, c-IAP1, c-IAP2 and NIAP are anti-apoptotic (Deveraux & Reed, 1999; Wang et al., 1998). TRPM-2 is anti-apoptotic in certain cell types (Miyake et al., 2000). There was no significant variation in the expression levels of xIAP, CART1 and CARF among various cell types. In contrast, c-IAP2 expression was observed only in MDA-MB-231, MDA-MB-436, MDA-MB-468 and HBL100 cells, all of which contain high levels of constitutive NF-κB DNA binding activity as shown in Table 1.

The c-IAP2 expression in these cells was further confirmed by Northern blot analysis (data not shown). TRAF1 expression was observed in MDA-MB-231 and MDA-MB-436 cells. Cell type-specific variation in TRPM2 expression was observed but did not correlate with NF-κB DNA binding activity. The expression levels of the anti-apoptotic gene c-IAP1, Mn-SOD and survivin were measured by Northern blotting (Jones et al., 1997; Li et al., 1998; Wang et al., 1998). While all cell lines expressed similar levels of c-IAP1 and survivin, Mn-SOD expression was higher in ERα-negative breast cancer cells with constitutive NF-κB DNA binding activity. Increased expression of Mn-SOD in ERα-negative breast cancer cells was further confirmed by Western blotting.

Differential screening of Atlas™ human cancer cDNA array (Clontech, Palo Alto, Calif.) using RNA from MDA-MB-231 cells and MDA-MB-231 cells modified to overexpress IκBα super-repressor (IκBαSR) (Wang et al., 1996) identified the anti-apoptotic gene DAD-1 as an NF-κB inducible gene (see below, data not shown) (Kelleher & Gilmore, 1997). However, DAD-1 expression did not correlate with constitutive NF-κB DNA binding activity. Taken together, these results suggest that constitutive activation of NF-κB leads to increased mRNA and/or protein levels of c-IAP2 and Mn-SOD in breast cancer cells.

EXAMPLE 2

IκBαSR Inhibits c-IAP2, Mn-SOD, TRAF1 and DAD-1 Expression in MDA-MB-231 Cells To further investigate whether c-IAP2 and Mn-SOD expression is dependent on NF-κB, MDA-MB-231 cells overexpressing IκBαSR were generated. Approximately 50% of colonies isolated using neomycin/G418 as a selection marker expressed IκBαSR. Most of these clones lost IκBαSR expression after continuous propagation in culture. No clones were obtained that were completely devoid of constitutive NF-κB DNA binding activity.

Three clones expressing IκBαSR (IκBαSR6, 8 and 10) and a clone containing retrovirus vector alone (LxSN11) were used for further studies. Constitutive NF-κB DNA activity in these clones was measured by EMSA using the general transcription factor SP-1 as an internal control. IκBαSR6, IκBαSR8 and IκBαSR10 cells displayed 20, 10 and 40% lower NF-κB DNA binding activity, respectively, than LxSN11 cells.

Similar results were obtained when EMSA was performed with nuclear extracts instead of whole cell extracts. Oligonucleotide competition studies and antibody supershift assays confirmed that IκBαSR inhibited DNA binding of p50:p65 heterodimeric complex of NF-κB. RNase protection assay revealed reduced TRAF1 and c-IAP2 expression in IκBαSR cells compared to LxSN11 cells. Furthermore, Mn-SOD and DAD-1, but neither c-IAP1 nor survivin, expression was reduced in IκBαSR cells compared to LxSN11 cells.

EXAMPLE 3

IκBαSR Cells are More Sensitive to Paclitaxel than LxSN Cells

Apoptosis by chemotherapeutic agents including paclitaxel involves activation of caspase 9 and caspase 3 (Thornberry & Lazebnik, 1998). Anti-apoptotic function of NF-κB is mostly due to Mn-SOD and c-IAP2 mediated inhibition of caspase 9 activation (Deveraux & Reed, 1999; Green & Reed, 1998). Also c-IAP2 inhibits the activity of caspase 3 (Deveraux & Reed, 1999). Recent studies have indicated that NF-κB alters cell cycle progression by modulating the expression of cell cycle regulatory genes (Guttridge et al., 1999; Hinz et al., 1999). Based on these observations, constitutively active NF-κB may decrease the sensitivity of cancer cells to chemotherapeutic agents whose activity is cell cycle-dependent.

After an initial survey of various chemotherapeutic drugs, paclitaxel was chosen for further study because of a consistent difference in response of LxSN11 and IκBαSR cells to this drug. Paclitaxel is a microtubule-stabilizing agent whose action is concentration dependent (Torres & Horwitz, 1998). At <9 nM drug concentration, paclitaxel acts by retarding or inhibiting progression through mitosis, thus altering microtubule dynamics. At these concentrations, cells exit mitosis aberrantly and fractionate into hypodiploid populations during cell cycle analysis (Torres & Horwitz, 1998). At >9 nM drug concentration, paclitaxel increases microtubule polymer mass, terminal G2/M arrest and cell death with a concomitant decrease in hypodiploid cells (Torres & Horwitz, 1998). At 3 nM paclitaxel concentration, approximately 30% of all cell types were hypodiploid. Hypodiploid population from all three cell types formed similar numbers of colonies when grown in culture suggesting that hypodiploid population not always represent apoptotic cells (data not shown). Increasing paclitaxel concentration to 5 nM did not alter the cell cycle distribution pattern of LxSN11 cells. In contrast, a large percent of IκBαSR cells were arrested at G2/M phase of the cell cycle. The percentage of cells at G2/M were 28.45±4.05, 70.37±14.9 and 62.1±13.1% for LxSN11, IκBαSR6 and IκBαSR10 cells, respectively. Only diploid cells were considered while calculating the percentage of cells in different phases of the cell cycle. These results suggest that genes activated by NF-κB reduce the ability of paclitaxel to induce G2/M arrest.

It was demonstrated previously that rates of paclitaxel-induced apoptosis directly correlate with number of G2/M arrested cells rather than number of hypodiploid cells (Torres & Horwitz, 1998). To determine whether increased G2/M arrest of IκBαSR cells is accompanied by increased apoptosis when compared to LxSN11 cells, a "cell death" ELISA was carried out (Kumar et al., 1996). To avoid loss of hypodiploid or other damaged cells during processing, the assay was performed with cell culture supernatants. After 18 h of paclitaxel treatment, there was only a marginal increase in apoptosis of LxSN11 cells, although a considerable number of cells were hypodiploid (FIG. 1). In contrast, a substantial increase in apoptotic death of IκBαSR10 cells was observed after paclitaxel treatment. Similar results were obtained when cells were incubated for 48 h with paclitaxel (FIG. 1). Note that there is an increased rate of spontaneous apoptosis in IκBαSR10 cells compared to LxSN11 cells, which further suggests that NF-κB activity is required for survival of MDA-MB-231 cells. Taken together, these results indicate that breast cancer cells with constitutively active NF-κB require a higher concentration of paclitaxel for G2/M arrest and possibly for apoptosis.

To determine whether lack of NF-κB in normal cells leads to altered sensitivity to paclitaxel, we compared the cell cycle distributions of paclitaxel-treated fibroblasts derived from p65−/−embryos with type littermate mouse embryos. Interestingly, paclitaxel had no effect on the cell cycle distribution of both wild type and p65−/−fibroblasts suggesting that paclitaxel-induced G2/M arrest is restricted to cancer cells (Table 2).

TABLE 2

The effect of paclitaxel on cell cycle progression of wild type and p65−/− fibroblasts. Cells were treated with indicated concentration of paclitaxel and cell cycle distribution was measured after 18 h of treatment. Consistent with this possibility, paclitaxel caused G2/M arrest of several other breast cancer cell lines (data not shown).

| | Wild type | | | p65−/− | | |
|---|---|---|---|---|---|---|
| Paclitaxel | G0/G1 | S | G2/M | G0/G1 | S | G2/M |
| — | 69 ± 2 | 12 ± 5 | 19 ± 3 | 47 ± 1 | 49 ± 1 | 4 ± 2 |
| 1 nM | 68 ± 4 | 20 ± 4 | 17 ± 8 | 47 ± 2 | 53 ± 1 | — |
| 3 nM | 70 ± 3 | 16 ± 1 | 14 ± 5 | 39 ± 6 | 61 ± 7 | 1 |
| 5 nM | 71 ± 3 | 16 ± 4 | 17 ± 6 | 47 ± 2 | 46 ± 6 | 14 |
| 10 nM | 73 ± 2 | 15 ± 2 | 16 ± 6 | 47 ± 2 | 48 ± 6 | 6 ± 4 |

EXAMPLE 4

Parthenolide Inhibits NF-κB DNA Binding Activity and Increases the Sensitivity of Breast Cancer Cells to Paclitaxel A. Curcumin, N-acetyl cysteine, pentoxyphylline, parthenolide, epigallocatechin gallate, Bay 11-7085 or MG-132 were evaluated for their ability to inhibit NF-κB DNA binding activity in breast cancer cells (Biswas et al., 1993; Hehner et al., 1998; Kumar et al., 1998; Lin et al., 1998; Pierce et al., 1997; Yang et al., 1998). Only parthenolide, MG132 and Bay 11-7085 inhibited NF-κB DNA binding activity in MDA-MB-231 cells. MDA-MB-231 cells were incubated with increasing concentrations (1, 2 and 5 μM) of parthenolide for 3 h. Whole cell extracts or nuclear extracts (5 μM only) from untreated and treated cells were subjected to EMSA with NF-κB or SP-1 probe. Parthenolide also inhibited constitutive NF-κB DNA binding activity in HBL100 cells (data not shown).

The effect of parthenolide on NF-κB DNA binding activity in cells treated with paclitaxel was then investigated. MDA-MB-231 cells pretreated with 5 μM parthenolide for 1 h were exposed to 50 nM paclitaxel for 1 h. EMSA was performed with whole cell extracts using NF-κB probe or SP-1 probe. Although paclitaxel has been shown to induce NF-κB in other cell types (Das & White, 1997), untreated and paclitaxel-treated MDA-MB-231 cells displayed a similar level of NF-κB DNA binding activity. Nonetheless, parthenolide inhibited NF-κB DNA binding activity in paclitaxel-treated cells.

Total RNA from MDA-MB-231 cells treated with 5 μM parthenolide for 0, 3, 6 or 24 hrs was subjected to Northern blotting and probed with Mn-SOD probe. Inhibition of NF-κB DNA binding activity by parthenolide also correlated with reduced Mn-SOD expression in MDA-MB-231 cells.

B. MDA-MB-231 and HBL100 cells were exposed to increasing concentrations of either paclitaxel or parthenolide and cell survival was measured after 18 h by an MTS assay. Half-maximal growth-inhibitory concentration ($IC_{50}$) was reached at 10 nM and 0.8 μM for paclitaxel and parthenolide, respectively, in HBL100 cells (data not shown). $IC_{50}$ of >30 nM and 2 μM for paclitaxel and parthenolide, respectively, was obtained for MDA-MB-231 cells (data not shown). For unknown reasons, only 30% of MDA-MB-231 cells were killed when incubated with 30 nM or higher concentrations of paclitaxel.

Figure 2A:
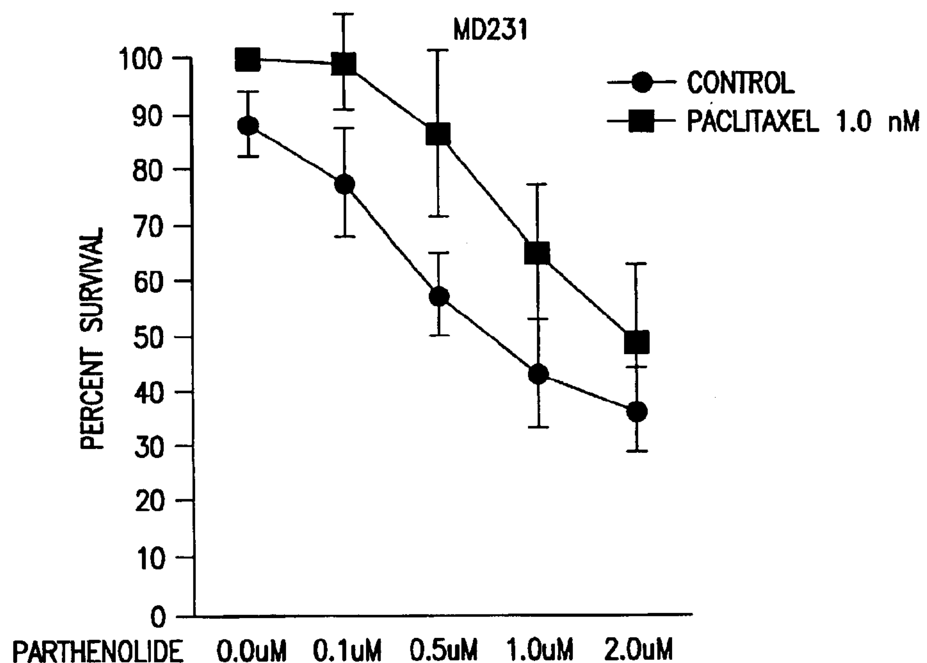
FIG. 2 is a graph depicting the increase in sensitivity of MD231 and HBL100 breast cancer cells to increasing concentrations of parthenolide, in the presence and absence of 1.0 nM paclitaxel.
Figure 2B:
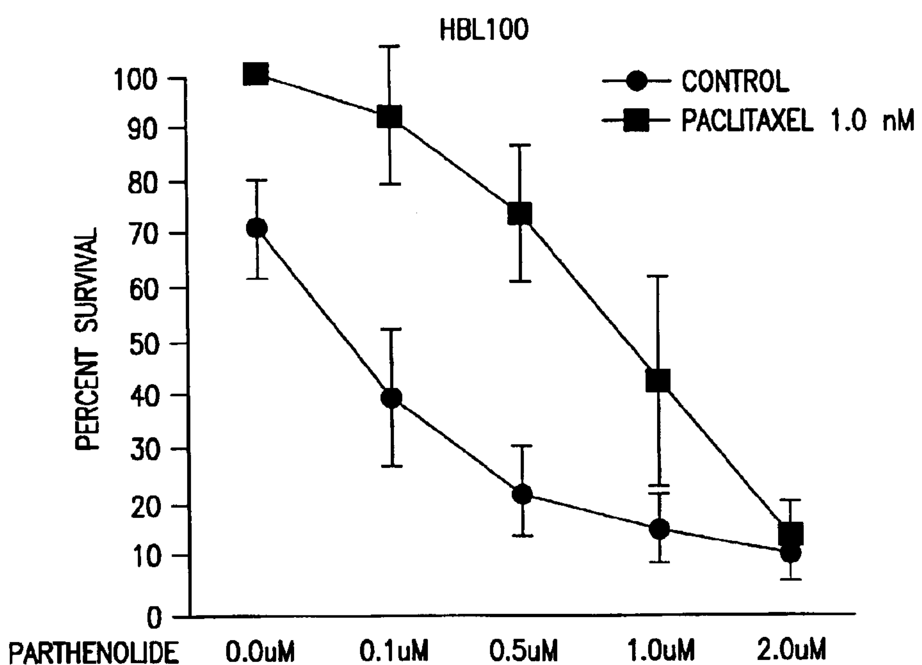

The effect of a combination of 1 nM paclitaxel and increasing concentrations of parthenolide was then studied. Parthenolide was added 4 h prior to paclitaxel addition. Cell death was measured 18 h after paclitaxel addition by MTS assay. Percent cell survival (average±standard deviation from three or more experiments) is shown in FIG. 2. The $IC_{50}$ of parthenolide decreased to <0.1 μM and approximately 0.8 μM for HBL100 and MDA-MB-231 cells, respectively (FIG. 2). As per the Isobole method, these results translate into >3.5 fold synergism with drug combination for HBL100 cells. The effect of combination therapy was more than additive for MDA-MB-231 cells.

Figure 3A:
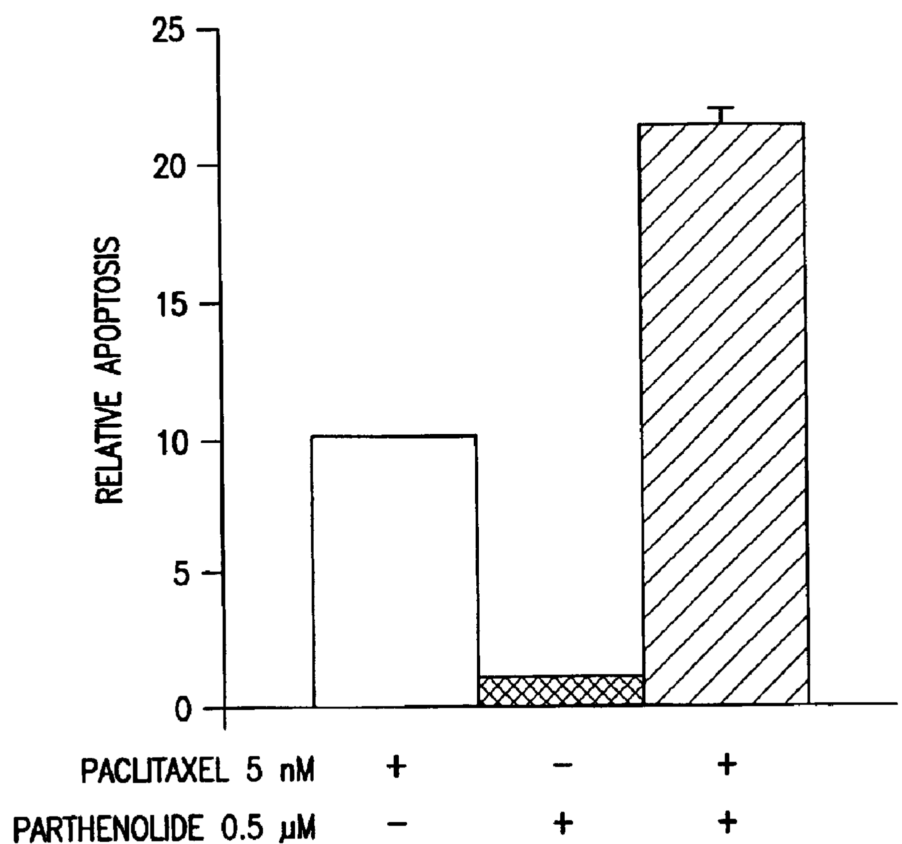
FIG. 3A is a graph depicting the relative apoptosis of HBL100 cells caused by paclitaxel and/or parthenolide.

C. To investigate whether the simultaneous exposure to paclitaxel and parthenolide leads to G2/M arrest and apoptosis, a cell cycle distribution analysis and "cell death ELISA" of untreated and treated HBL100 cells was carried out. Parthenolide had no effect on the cell cycle distribution of HBL100 cells (data not shown). Cells treated with either paclitaxel alone or in combination with parthenolide were arrested at G2/M, although a synergistic effect of drug combination on G2/M arrest was observed in only some experiments (data not shown). HBL100 cells were treated with indicated drugs and cell death was measured by ELISA after 18 h of paclitaxel addition. In combination therapy, parthenolide was added 4 h before paclitaxel treatment. Apoptosis in paclitaxel treated cells was set as 10 units and relative apoptosis in cells treated with either parthenolide alone or both paclitaxel and parthenolide is shown. Paclitaxel alone induced apoptosis to a certain degree whereas parthenolide was ineffective (FIG. 3A). A synergistic increase in apoptosis was observed when cells were exposed to a combination of parthenolide and paclitaxel (FIG. 3A).

Figure 3B:
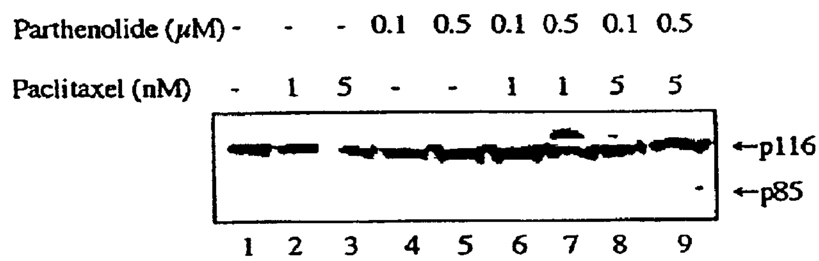
FIG. 3B is a photocopy of a Western blot showing PARP cleavage products in HBL100 cells treated with paclitaxel and/or parthenolide.

To further confirm that combination therapy induces apoptosis, the cleavage of PARP from 116 kDa to 85 kDa protein by caspases was used (Panvichian et al., 1998). Cells were lysed 24 h after paclitaxel addition, and the lysate was examined for uncleaved (p116) and cleaved PARP (p85) by Western blotting (FIG. 3B). No PARP cleavage product was observed when $5 \times 10^5$ HBL100 cells were incubated with either paclitaxel (1 nM and 5 nM) or parthenolide (0.1 $\mu$M and 0.5 $\mu$M) alone (FIG. 3B). In contrast, PARP cleavage product was detected when cells were treated with a combination of 5 nM paclitaxel and 0.5 $\mu$M parthenolide. Note that PARP cleavage was not detected in cells treated with low concentrations of paclitaxel and parthenolide, although cell death at these concentrations was measurable in MTS assays. This discrepancy is most likely due to differences in the sensitivity of the two assays. Nevertheless, these results suggest that inhibition of NF-κB activity by parthenolide increases the rate of apoptotic cell death by paclitaxel.

As demonstrated by Examples 1–4, constitutive NF-κB DNA binding activity in breast cancer cells correlates with increased expression of the anti-apoptotic genes c-IAP2 and Mn-SOD. Also, constitutive NF-κB DNA binding has been shown to correlate with increased expression of the prometastatic genes urokinase plasminogen activator, IL-6 and IL-8 (Newton et al., 1999). These observations are significant because constitutive NF-κB DNA binding has been observed in 65% of primary breast cancers (Sovak et al., 1997).

These examples demonstrated that c-IAP2 is a major NF-κB inducible gene in breast cancer cells. Preliminary evidence obtained using reverse transcriptase-polymerase chain reaction analysis of tumor RNA indicated that c-IAP2 is overexpressed in primary breast cancers. c-IAP2 is a more potent inhibitor of caspase 3 and caspase 7 activity than c-IAP1, and can suppress apoptosis induced by a variety of stimuli including TNF, Fas, menadione, staurosporine, etoposide, paclitaxel and growth factor withdrawal (Deveraux & Reed, 1999).

Previously, it was reported that reduced expression of the pro-apoptotic gene Bax is responsible for chemoresistance in breast cancer (Bargou et al., 1996). Bax activates caspase-dependent and caspase-independent apoptotic pathways (Xiang et al., 1996). Constitutively active NF-κB through c-IAP2 may confer chemoresistance even in tumors that express Bax, because c-IAP2 can block the caspase-dependent apoptotic pathway (Deveraux & Reed, 1999).

Paclitaxel is a commonly used chemotherapeutic agent in both the adjuvant and metastatic settings. Thus, c-IAP2 expression can provide a predictor of response to this important agent and its analogs.

Mn-SOD appears to have a dual role in cancer. Mn-SOD can reduce oxidative stress, protect against DNA damage and prevent initiation of cancerous mutation (Oberley & Oberley, 1997). Consistent with this possibility, the incidence of breast cancer is higher in premenopausal women who have inherited the polymorphic variant of Mn-SOD with reduced biological activity (Ambrosone et al., 1999). However, Mn-SOD may also protect cancer cells from chemotherapy induced oxidative stress and apoptosis (Manna et al., 1998). Indeed, overexpression of Mn-SOD alone is sufficient to confer resistance to okadaic acid, $H_2O_2$, and paclitaxel but not vincristine, vinblastine and daunomycin induced apoptosis of breast cancer cells (Manna et al., 1998). These observations raise the possibility that NF-κB may also have a dual role in mammary epithelial cells. By upregulating Mn-SOD and other anti-oxidant genes, NF-κB may protect normal mammary epithelial cells from oxidative stress and DNA damage. In cancer cells, however, these anti-oxidant gene products may protect against chemotherapy induced oxidative stress and apoptosis.

It was reported recently that caspases active during apoptosis cleave NF-κB and attenuate anti-apoptotic response (Levkau et al., 1998). Therefore, although several chemotherapeutic agents including paclitaxel induce NF-κB (Das & White, 1997), it is less likely that activated NF-κB can mount an anti-apoptotic response. However, NF-κB can protect against chemotherapeutic agents if it is constitutively active and, as a consequence, cells constitutively express Mn-SOD and c-IAP2. Therefore, IκBαSR or NF-κB inhibitors may be useful in overcoming chemotherapeutic resistance of only those cells that contain constitutively active NF-κB. Consistent with this possibility, IκBαSR overexpression in HPB, HCT116, MCF-7, and OVCAR-3 cells, all of which lack constitutively active NF-κB, did not increase the sensitivity to paclitaxel (Bentires-Aji et al., 1999).

A survey of a number of known inhibitors of NF-κB revealed that parthenolide can function similarly to IκBαSR by increasing the sensitivity of breast cancer cells to paclitaxel. However, the degree of synergism appears to be dependent on the cell type, as HBL100 cells were more sensitive to the combined treatment than MDA-MB-231 cells. The cell type-specific effect may be related to differences in the stability of parthenolide within cells or the number of cell survival pathways that are active in a particular cell type.

The NF-κB-mediated survival pathway is believed to be the major cell survival pathway in HBL100 cells, whereas NF-κB-independent survival pathways provide partial protection to MDA-MB-231 cells. This possibility is supported by other in vitro observations that MDA-MB-231 cells represent a more "advanced cancer cell type" (with respect to growth in nude mice) than HBL100 cells (Price et al., 1990; Sommers et al., 1994). In cancer types that are dependent on NF-κB, a combination of parthenolide and chemotherapeutic drugs may be beneficial. Such an approach is less likely to be toxic to normal cells.

EXAMPLE 5

Parthenolide Inhibits Prostate Cancer Cell Proliferation

Two prostate cancer cell lines (hormone sensitive, LNCaP and hormone-resistant PC-3) were cultured and treated with 0.5, 1.0, 2.5 and 5 $\mu$M parthenolide. Mobility shift gel electrophoresis assay was performed on the prostate cancer cells after treatment with parthenolide for three hours. Proliferation assays were performed using a 96 well plate with cell viability assesses utilizing the MTS/PMS assay (see Example 6). Inhibition was compared with a solvent control.

Figure 4A:
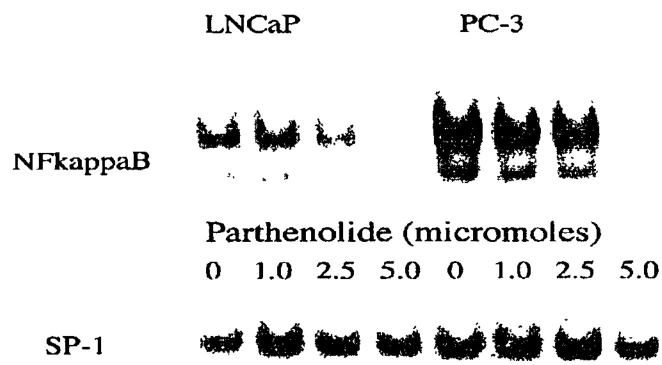
FIG. 4A is a photocopy of an EMSA gel showing the effect of parthenolide on NF-κB binding in prostate cancer cell lines.
Figure 4B:
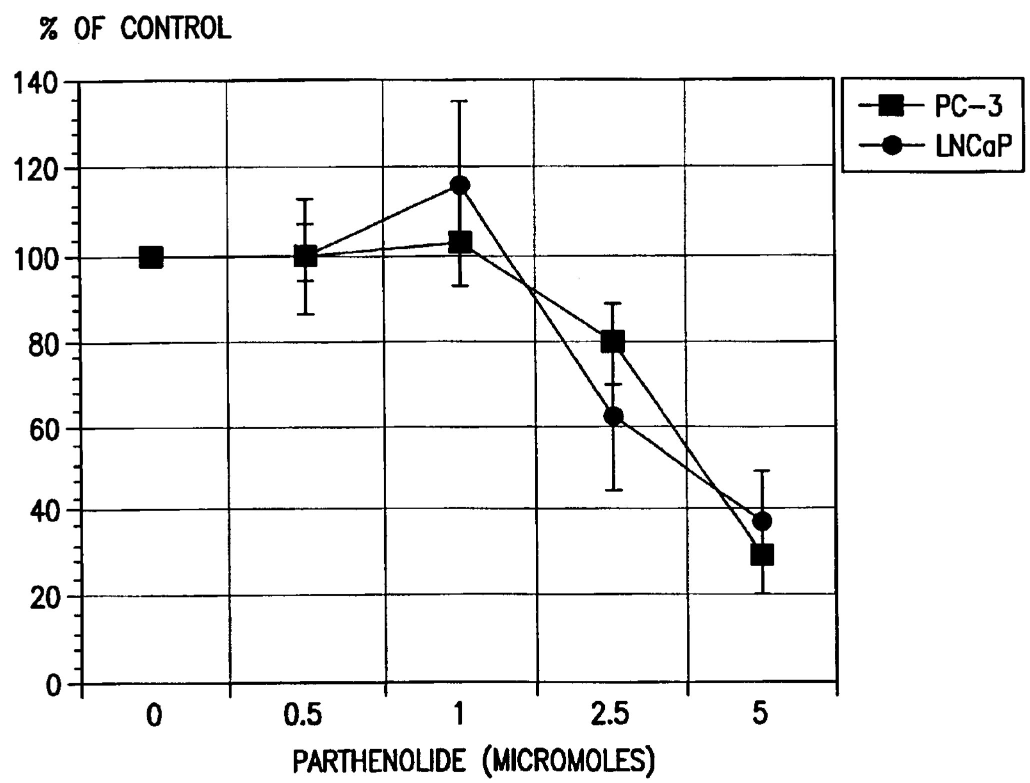
FIG. 4B is a graph depicting inhibition of prostate cancer cell inhibition by parthenolide.

Constitutive NF-κB DNA binding was present in both cell lines, but greater DNA binding was observed in the hormone resistant cell line, PC-3, as shown in FIG. 4A. Parthenolide induced a dose-dependent decrease in DNA binding as shown in FIG. 4B. There was no effect observed at 1 micromolar of parthenolide and almost complete inhibition of DNA binding with 5 micromolar. These results closely paralleled the observations from the proliferation assays, as the $IC_{50}$ for LNCaP and PC-3 was 3.9 $\mu$M and 4.1 $\mu$M respectively.

NF-κB is constitutively active in both a hormone-sensitive and hormone-resistant prostate cancer cell line. The greater binding in the hormone-resistant cell line suggests that this transcription factor may be involved in the development of hormone resistance. Inhibition of this transcription factor with parthenolide results in an inhibition of prostate cancer cell proliferation.

EXAMPLE 6

Anti-angiogenic Activity of Parthenolide

A. Materials

Human umbilical venous endothelial cells (HUVECs) (Clonetics, San Diego, Calif.) were cultured in EGM-2 media (Clonetics, San Diego, Calif.) and harvested after having undergone no more than five passages. Parthenolide powder (Sigma Chemical Co., St. Louis, Mo.) was added at varying concentrations to a proliferation and a capillary formation assay, electromobility gel shift assay and in an in vivo assay. RhuMAb VEGF (provided by Genentech, South San Francisco, Calif.) was used in the electromobility gel shift assay. VEGF (Chemicon International, Temecula, Calif.) and basic Fibroblast Growth Factor, bFGF (R & D Systems, Minneapolis, Minn.) were added to the assays in doses that have been shown in vitro to induce the maximal amount of HUVEC endothelial cell proliferation. Thrombin, bovine fibrinogen and aprotinin (all from Sigma Chemical Co., St. Louis, Mo.) were used for the formation of a fibrin clot. Microcarrier beads consisting of thin layer denatured collagen chemically coupled to a matrix of cross-linked dextran (175 microns, Cytodex™3, Amersham Pharmacia, Biotech AB, Uppsale, Sweden) were employed as the base for the capillary formation. This assay has been shown to induce capillaries with identifiable lumens. The MTS/PMS system (Promega, Madison, Wis.) was used to assess cell viability for the proliferation assay.

B. Methods

1. Proliferation

HUVECs were plated in a 96-well U-bottomed plate (Becton Dickinson Labware, Franklin Lakes, N.J.) at a concentration of 10,000 cells per 50 microliters (μL) of media and incubated in 5% $CO_2$ at 37° C. for 48 hours. Varying drug concentrations in 50 μL of media were added to the media and this mixture was added to each well within one hour of the HUVECs being seeded. The proliferation experiments were performed with and without stimulation by the addition of VEGF (60 ng/mL) and bFGF (20 ng/mL). These factors in high doses were chosen to partially simulate the tumor microenvironment. Colorimetric readings were obtained using the MTS/PMS system and an ELISA plate reader. The readings obtained for each concentration tested were from an average of eight wells. Each experiment was expressed as a percentage of the solvent control and completed at least three times with consistent results. The results presented are an average of at least three experiments.

2. Endothelial Cell Capillary Formation

Two hundred milligrams of microcarrier beads suspended in PBS were autoclaved and then added to HUVECs at a concentration of 30 HUVECs per microcarrier bead. Microcarrier beads and cells were added to a siliconized petri dish and rocked at 37° C. in 5% $CO_2$ for 48 hours. The HUVEC coated microcarrier beads were transferred to a fibrin clot solution. Fibrinogen was dissolved at 2.5 mg/mL in PBS with 0.15 U/mL of aprotinin. Approximately 20 HUVEC coated microcarrier beads were added to each well of a 12 well plate and then thrombin (0.625 U/mL) was added to form a gelatinous clot. Media (1.5 mLs) with 1% human serum and aprotinin (0.15 U/mL) were added to the top of each clot. The addition of VEGF (60 ng/mL) and bFGF (20 ng/mL) was required to ensure robust capillary formation. There was minimal capillary formation without stimulation and therefore all results reported are with stimulation. The drugs to be tested were also added to the top layer. Capillary formation was then quantified after four days: every capillary greater than the radius of the bead was scored and the average number of tubules for each bead per well was determined. The results were expressed as a fraction of the positive control. The experiments were repeated at least three times and the results presented are the average of at least three experiments.

3. Electromobility Gel Shift Assay

HUVECs were plated on 100 mm plates and harvested in an exponential growth phase. Drugs, antibodies and cytokines were added three hours prior to harvesting—bFGF alone at 50 ng/mL, VEGF alone at 100 ng/mL, rhuMAb VGEF at 10 mg/mL, bFGF plus rhuMAb VEGF; VEGF plus rhuMAb VEGF and parthenolide at doses ranging from 2 to 10 μM. Cellular extracts were made and incubated with a radiolabelled NF-κB probe for 30 minutes at 25° C. This protein probe binds to the NF-κB DNA binding site in the promoter region of the immunoglobulin gene. The mixture was then electrophoresed. Specific NF-κB binding to DNA was identified by the presence of a signal seen at autoradiography. The protein-DNA complex was slower to migrate whereas unbound DNA and protein migrated off the gel. The specificity of the drug inhibiting NF-κB DNA binding was verified by the use of the SP-1 probe as a control.

4. Matrigel Plug Assay

Matrigel was prepared on ice and incubated with 100 ng/mL of VEGF or 50 ng/mL of bFGF. Under light anaesthesia with isofluorane, 0.3 mL of matrigel was injected into the left and right flanks of each mouse. The VEGF containing matrigel plug was placed on the left and the bFGF plug was placed on the right. On the second day after the plugs were inserted, the mice were treated daily for 14 days by oral gavage. Parthenolide was dissolved in 100% alcohol at 40 mg/mL and then diluted in PBS so that each mouse received their assigned dose in 100 μL of solution. There were 10 mice per cohort and the treatments were (1) 20% alcohol in PBS—control; (2) 0.4 mg/mL; (3) 4.0 mg/mL and 40 mg/mL. These doses are non-toxic when given for one month (no weight loss, no lethargy). The mice were sacrificed and the plugs harvested on the $14^{th}$ day. The hemoglobin content was measured using the "Drabkins assay". The weight of each plug was determined and the plugs were dissolved in 100 ml of water per mg of matrigel plug. The mixture was placed in duplicate in a 96 well plate and incubated for 24 hours. The optical density was determined and the average for each pair was determined. The optical density is a measure of the hemoglobin content and the median for each cohort was determined with the standard error also calculated.

C. Results

1. In vitro

Figure 5:
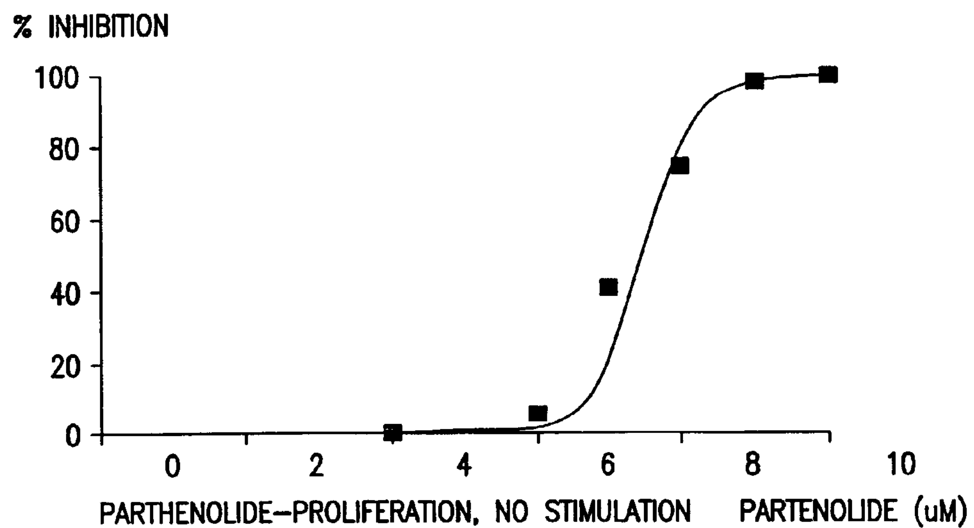
FIG. 5 is a graph depicting the inhibition of HUVECs by parthenolide.
Figure 6:
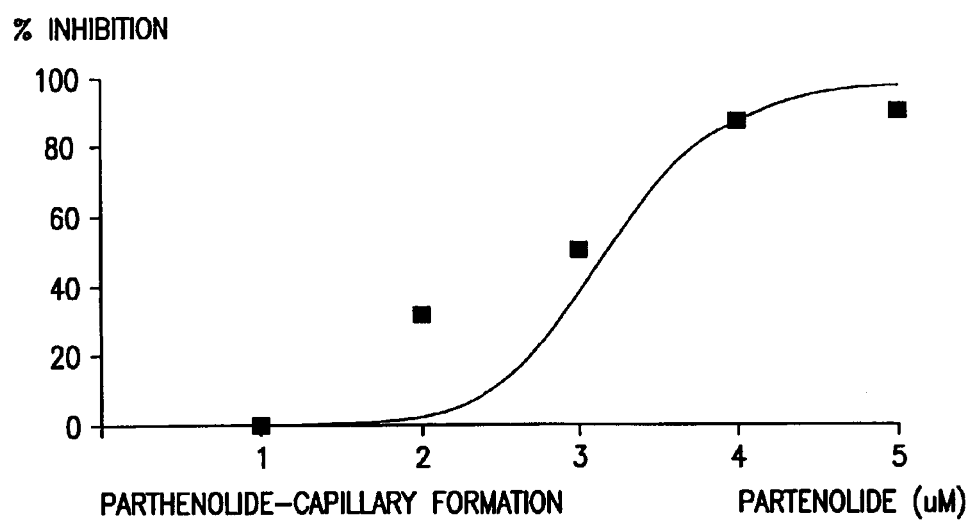
FIG. 6 is a graph depicting the inhibition of capillary formation by HUVECs by parthenolide.

Parthenolide inhibited HUVEC proliferation. This inhibition was not substantially altered by stimulation with survival factors—$IC_{50}$ was 7.5 μM with unstimulated media (FIG. 5) and 8.6 μM with stimulated media. Capillary formation was inhibited with a lower $IC_{50}$ of 3.2 μM (FIG. 6).

2. In vivo

Figure 7:
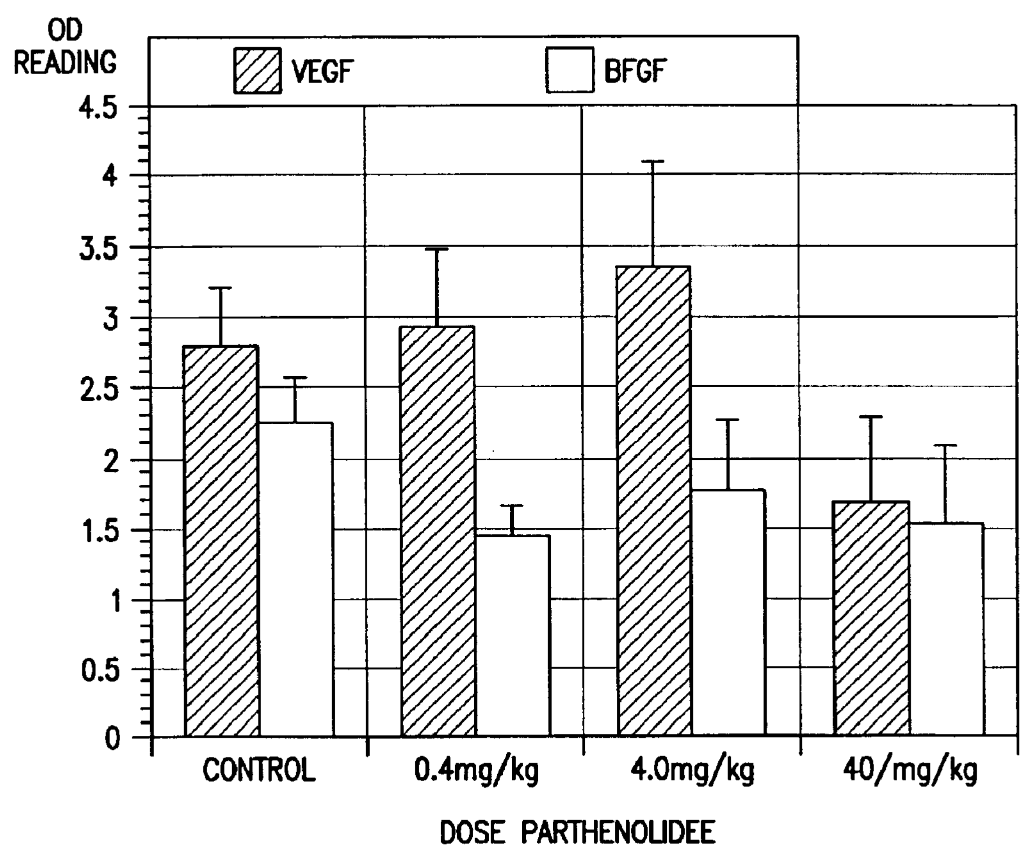
FIG. 7 is a graph depicting the effect of parthenolide on in vivo-induced angiogenesis.

The matrigel plug assay revealed that parthenolide had an effect on in vivo angiogenesis. There was a 40% reduction in bFGF-induced angiogenesis at the 0.4 mg/mL dose which was not increased by the higher doses (FIG. 7). In contrast, it required 40 mg/kg of parthenolide to inhibit VEGF-induced angiogenesis by 40%.

3. Electromobility Gel Shift Assay

Figure 8:
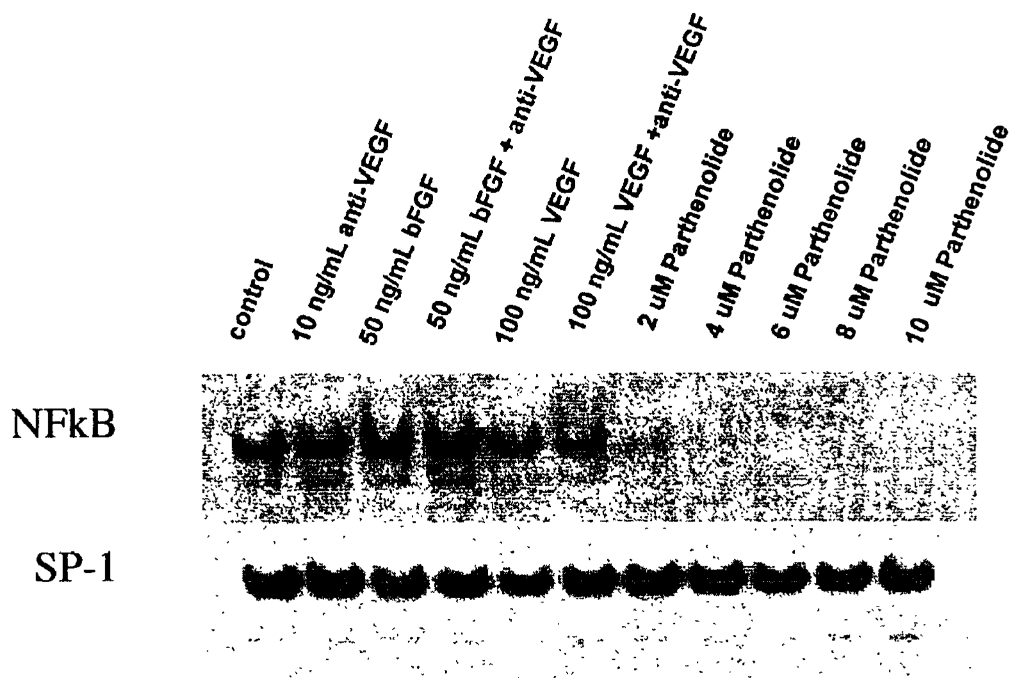
FIG. 8 is a photocopy of an electromobility gel shift assay gel demonstrating the effect of parthenolide on NF-κB DNA binding.

As depicted in FIG. 8, bFGF induced greater DNA binding than VEGF. The bFGF effect was not altered by rhuMAb-VEGF. RhuMAb-VEGF did not alter NF-κB DNA binding. When controlled for loading, VEGF did not alter baseline NF-κB DNA binding. Parthenolide was able to markedly decrease but not eliminate the NF-κB DNA binding at baseline at 2 μM and 4 μM. At doses of 6 μM and higher, there was complete inhibition of DNA binding.

C. Discussion

Angiogenesis has been found to be a critical factor in many physiological processes such as embryonic development and wound healing as well as in pathological processes, which include the neovascularity that can cause blindness in diabetic retinopathy and the induction of a new blood supply to support the growth of cancerous growth. Inhibition of the latter process by anti-angiogenic agents has been shown to induce tumor regression. One such agent is rhuMAb VEGF which can induce tumor regression in 20% of patients with breast cancer.

The data presented in this example demonstrates that actively proliferating venous endothelial cells have constitutive NF-κB DNA binding. This inhibition of NF-κB DNA binding by parthenolide coincides with inhibition of endothelial cell proliferation, capillary formation and in vivo angiogenesis as measured by hemoglobin content in a matrigel plug. Therefore, parthenolide may be a potent anti-angiogenic agent for the treatment of angiogenic-based diseases.

REFERENCES

S. F. Amato et al., *Cancer Res.,* 58, 241 (1998).

L. B. Ambrosone et al., *Cancer Res.,* 59, 602 (1999).

P. A. Baeuerle et al., *Annu. Rev. Immunol.,* 12, 141 (1994).

N. Baldini, *Nat. Med.,* 3, 378 (1997).

R. C. Bargou et al., *J. Clin. Invest.,* 100, 2961 (1997).

R. C. Bargou et al., *J. Clin. Invst.,* 97, 2651 (1996).

A. A. Beg et al., *Science,* 274, 782 (1996).

M. Bentires-Aji et al., *Cancer Res.,* 59, 811 (1999).

K. C. Berenbaum, *Adv. Cancer Res.,* 25, 269 (1981).

P. Bhat-Nakshatri et al., *Proc. Natl. Acad. Sci. USA,* 95, 6971 (1998).

D. K. Biswas et al., *J. Acquir. Immune Defic. Syndr.,* 6, 778 (1993).

M. V. Blagosklonny et al., *Cancer Res.,* 56, 1851 (1996).

M. V. Blagosklonny et al., *Cancer Res.,* 55, 4623 (1995).

P. M. Bork et al., *FEBS Lett.,* 402, 85 (1997).

L. Cassimeris, *Curr. Opin. Cell. Biol.,* 11, 134 (1999).

P. C. Cogswell et al., *Oncogene,* 19, 1123 (2000).

K. C. Das et al., *J. Biol. Chem.,* 272, 14914 (1997).

Q. L. Deveraux et al., *Genes Dev.,* 13, 239 (1999).

J. D. Dignam et al., *Nucleic Acids Res.,* 11, 1475 (1983).

G. Dong et al., *Cancer Res.,* 59, 3495 (1999).

C. Ferlini et al., *Br. J. Cancer* 75, 884 (1997).

D. E. Fisher, *Cell,* 78, 539 (1994).

K. Fukuda et al., *Planta Med.,* 65, 381 (1999).

R. Galien et al., *Nucleic Acids Res.,* 25, 2424 (1997).

D. K. Giri et al., *J. Biol. Chem.,* 273, 14008 (1998).

D. R. Green et al., *Science,* 281, 1309 (1998).

R. J. Grumont et al., *Genes Dev.,* 13, 400 (1999).

A. Gutman et al., *EMBO J.,* 9, 2241 (1990).

D. C. Guttridge et al., *Mol. Cell. Biol.,* 19, 5785 (1999).

S. Habtemariam, *Planta Med.,* 64, 683 (1998).

S. P. Hehner et al., *J. Biol. Chem.,* 273, 1288 (1998).

S. P. Hehner et al., *J. Immunol.,* 163, 5617 (1999).

M. Hinz et al., *Mol. Cell. Biol.,* 19, 2690 (1999).

F. Jiang et al., *J. Pathol.,* 185, 382 (1998).

P. L. Jones et al., *Mol. Cell. Biol.,* 17, 6970 (1997).

D. J. Kelleher et al., *Proc. Natl. Acad. Sci. USA,* 94, 4994 (1997).

A. Kumar et al., *Biochem. Pharmacol.,* 55, 775 (1998).

R. Kumar et al., *Clin. Cancer Res.,* 2, 1215 (1996).

H. H. Lee et al., *Proc. Natl. Acad. Sci. USA,* 96, 9136 (1999).

O. Legrand et al., *Blood,* 91, 4480 (1998).

B. Levkau et al., *J. Exp. Med.,* 187, 579 (1998).

B. Levkau et al., *Nature Cell. Biol.,* 1, 227 (1999).

F. Li et al., *Nature,* 396, 580 (1998).

Z. P. Lin et al., *Cancer Res.,* 58, 3059 (1998).

Y. H. Ling et al., *J. Biol. Chem.,* 273, 18984 (1998).

L. A. Liotta et al., *Cell,* 64, 327 (1991).

G. Lyss et al., *J. Biol. Chem.,* 273, 33508 (1998).

S. K. Manna et al., *J. Biol. Chem.,* 273, 13245 (1998).

A. D. Miller et al., *Biotechniques,* 7, 980, 984, 989 (1989).

H. Miyake et al., *Cancer Res.,* 60, 170 (2000).

J. J. Murphy et al., *Lancet,* 2, 189 (1988).

H. Nakshatri, *J. Biol. Chem.,* 274, 18827 (1999).

H. Nakshatri et al., *Mol. Cell. Biol.,* 17, 3629 (1997).

T. R. Newton et al., *J. Biol. Chem.,* 274, 18827 (1999).

T. D. Oberley et al., *Histol. Histopathol.,* 12, 525 (1997).

R. Panvichian et al., *Cancer Res.,* 58, 4667 (1998).

J. W. Pierce et al., *J. Biol. Chem.,* 272, 21096 (1997).

J. E. Price et al., *Cancer Res.,* 50, 717 (1990).

J. Y. Reuther et al., *Genes Dev.,* 12, 968 (1998).

R. L. Shattuck-Brandt et al., *Cancer Res.,* 57, 3032 (1997).

S. -C. Shen et al., *Cell Growth Differ.,* 9, 23 (1998).

C. L. Sommers et al., *Breast Cancer Res. Treat.,* 31, 325 (1994).

M. A. Sovak et al., *J. Clin. Invest.,* 100, 2952 (1997).

G. E. Sonenshein, *J. Clin. Invest.,* 100, 2952 (1997).

N. A. Thornberry al., *Science,* 281, 1312 (1998).

K. Torres, *Cancer Res.,* 58, 3620 (1998).

D. J. Van Antwerp et al., *Science,* 274, 787 (1996).

C. Y. Wang et al., *Nat. Med.,* 5, 412 (1999a).

C. Y. Wang et al., *Mol. Cell. Biol.,* 19, 5923 (1999b).

C. Y. Wang et al., *Science,* 281, 1680 (1998).

C. Y. Wang et al., *Science,* 274, 784 (1996).

J. Xiang et al., *Proc. Natl. Acad. Sci. USA,* 93, 14559 (1996).

F. Yang et al., *J. Nutr.,* 128, 2334 (1998).

M. J. Yin et al., *Nature,* 396, 77 (1998).

E. Zandi et al., *Mol. Cell. Biol.,* 19, 4547 (1999).

W. -X. Zong et al., *Genes Dev.,* 13, 382 (1999).

All of the publications, patents and patent applications cited hereinabove are incorporated by reference herein, as though fully set forth.

What is claimed is:

1. A method of reducing viability of cancer cells comprising:

a) identifying cancer cells having constitutively active NF-κB; and b) contacting the cancer cells with an amount of parthenolide effective to reduce their viability.

2. A method of increasing susceptibility of cancer cells to a chemotherapeutic agent comprising:

a) identifying cancer cells having constitutively active NF-κB; and b) contacting the cells with an effective sensitizing amount of parthenolide.

3. The method of claim 1 or 2 wherein step (a) further comprises identifying cancer cells that overexpress c-IAP2.

4. The method of claim 1 or 2 wherein the cancer cells are human cancer cells.

5. The method of claim 4 wherein the parthenolide is administered to a human cancer patient.

6. The method of claim 5 wherein the cancer patient is undergoing treatment with a second chemotherapeutic agent.

7. The method of claim 5 wherein the cancer patient is afflicted with a solid tumor.

8. The method of claim 7 wherein the tumor is breast cancer.

9. The method of claim 8 wherein the patient is further treated with paclitaxel.

10. The method of claim 7 wherein the tumor is prostate cancer.

11. The method of claim 5 wherein the cancer has been treated by surgical removal and/or radiation.

12. The method of claim 5 wherein the parthenolide is administered orally.

13. The method of claim 5 wherein the amount of parthenolide is effective to inhibit angiogenesis by said cancer cells.

14. The method of claim 1 or 2 wherein the cancer cells are mammalian cancer cells.

15. The method of claim 1 or 2 wherein the cancer cells are breast cancer cells.

16. The method of claim 1 or 2 wherein the cancer cells are prostate cancer cells.

17. The method of claim 1 or 2 wherein the cancer cells are pancreatic cancer cells.

18. The method of claim 1 or 2 wherein the cancer cells are lung cancer cells.

19. The method of claim 1 or 2 wherein the cancer cells are bladder cancer cells.

* * * * *